United States Patent
Cheh (10) Patent No.: US 7,752,769 B1
(45) Date of Patent: Jul. 13, 2010

(54) SELF-APPLIED MEASUREMENT KIT FOR A HAIR REPLACEMENT MOLD

(76) Inventor: Byung Joe Cheh, 2361 Achilles Dr., Los Angeles, CA (US) 90046

( * ) Notice: Subject to any disclaimer, the term of this patent is extended or adjusted under 35 U.S.C. 154(b) by 0 days.

(21) Appl. No.: 12/464,810

(22) Filed: May 12, 2009

(51) Int. Cl.
*A61B 5/00* (2006.01)
*A61B 1/00* (2006.01)
*G01B 3/34* (2006.01)

(52) U.S. Cl. ........................... 33/514.2; 33/512
(58) Field of Classification Search ........... 33/511–512, 33/514.1, 514.2, 1 BB, 758, 759, 770
See application file for complete search history.

(56) References Cited

U.S. PATENT DOCUMENTS

| | | | | |
|---|---|---|---|---|
| 2,670,743 A * | 3/1954 | Gabaer | .................. | 132/223 |
| 2,953,140 A * | 9/1960 | Goff | .................. | 132/250 |
| 4,106,515 A * | 8/1978 | Miller | .................. | 132/214 |
| 5,140,978 A * | 8/1992 | Sirninger | .................. | 601/18 |
| 6,564,463 B1 * | 5/2003 | Panz | .................. | 33/512 |
| 2004/0134084 A1 * | 7/2004 | Vanneste | .................. | 33/512 |
| 2007/0067033 A1 * | 3/2007 | Bonati | .................. | 623/15.11 |
| 2007/0251536 A1 * | 11/2007 | Kupitz | .................. | 132/53 |
| 2009/0266373 A1 * | 10/2009 | Kupitz | .................. | 132/54 |

* cited by examiner

*Primary Examiner* — Yaritza Guadalupe-McCall
(74) *Attorney, Agent, or Firm* — John K. Park; Park Law Firm (57) ABSTRACT

A self-applied measurement kit for a hair replacement mold is provided. The kit comprises one shape wire, two side wires, one shape sheet and one domed support pad. The shape wire is adjusted to fit the desired hair boundaries and to be fixed on the head. The two side wires are draped downward toward the chin of the user and tied, so as to fix the shape wire in place. The shape sheet covers the head wearing the shape wire, so as to imprint the shape of the head, and the shape sheet is pinched to imprint the position and shape of the shape wire. The domed support pad keeps the molded shape wire and shape sheet from deforming. The two side wires facilitates fixing the shape wire on the head and imprinting the shape of the head and the shape wire fixed in place fitting the desired hair boundaries.

19 Claims, 9 Drawing Sheets

SELF-APPLIED MEASUREMENT KIT FOR A HAIR REPLACEMENT MOLD

BACKGROUND OF THE INVENTION

The present invention relates to a self-applied measurement kit for a hair replacement mold.

There are many causes of hair loss, some genetic and some due to injury or illness. For many people, substantial hair loss can be considered a disfigurement, and a social or business barrier. Thus, over the past several decades, a broad spectrum of hair loss remedies has emerged. At one end are simple chemical remedies. If these are ineffective, surgical transplants are available, if there are sufficient donor hair follicles to supply the needs of transplanting. However, such procedures require significant time and money. As such, many people opt instead for non-surgical hair replacement methods such as hair pieces or wigs. While hair pieces or wigs can be made of synthetic fiber, the most natural-look requires custom-fit pieces made from human hair. Modern hair piece design is done in several stages. First, the hair piece maker examines the client to measure the shape of the head and the size of the bald/thinning region; the result is the simple mold that will be cast and upon which the hair piece will be built. The next step involves the process of assembling and weaving the hairs into a substrate. This process is very labor intensive and tedious; hence, the process has gravitated toward Asia, where labor costs are less. For a hair piece or wig designer in the U.S., this means sending very exacting specifications overseas.

Accordingly, the need for a self-applied measurement kit for a hair replacement mold exists. This invention cuts down on the time, cost, travel, and labor required by modern hair piece design: clients can now create the simple mold themselves, without having to visit the hair piece designer.

SUMMARY OF THE INVENTION

The present invention works to solve the disadvantages of the prior art.

An objective of the invention is to provide a self-applied measurement kit for a hair replacement mold.

Another object of the invention is to provide a self-applied measurement kit for a hair replacement mold that enables a user to self-prepare and self-measure the specifications for the molds used to create hair pieces, wigs, and hair piece replacements.

Still another object of the invention is to provide a method for using the self-applied measurement kit for a hair replacement mold.

An aspect of the invention provides the self-applied measurement kit, comprising: (a) one shape wire; (b) two side wires; (c) one shape sheet; (d) one domed support pad.

The shape wire is configured to be adjusted to fit the desired hair boundaries on a user's head and to be fixed to the head.

The two side wires, each of which extend downward from a side portion of the shape wire, are configured to be draped downward over and tied down under the chin of the user, so as to fix the shape wire in place to the user's head. The two side wires facilitate fixing the shape wire to the user's head such that the shape wire imprints the shape of the head and the desired hair boundaries on the shape sheet.

The shape sheet is configured to cover the user's head, and is placed on top of the shape wire, so as to imprint the shape of the head. The shape sheet is pinched over the shape wire so as to imprint the position and shape of the shape wire.

The domed support pad is configured to support and keep the shaped shape wire and shape sheet from deforming.

The shape wire may comprise solid metal and twisted strands of two or more solid metal wires. In certain embodiments of the invention, the shape wire may be comprised of chenille strands.

The two side wires may comprise of soft metal. In certain embodiments of the invention, one of the two side wires may comprise iron and copper.

The shape sheet may comprise a malleable metal sheet. In certain embodiments of the invention, the shape sheet may comprise aluminum foil.

The domed support pad may comprise plastic, rubber, or other hard, solid material.

The self-applied measurement kit may further comprise a rear tube provided around an overlapped portion of the shape wire and configured to hold and prevent the overlapped portion from slipping or loosening with a predetermined resistance.

The overlapped portion may be disposed at the rear of the user's head.

The self-applied measurement kit may further comprise two side tubes, each of which being provided around an overlapped portion of the shape wire and one of the side wires and configured to hold and prevent the overlapped portion from slipping or loosening with a predetermined resistance.

The overlapped portions may be disposed above the user's ears.

Another aspect of the invention provides a method for using the self-applied measurement kit for a hair replacement mold.

The method comprises steps of: putting a shape wire on a user's head; adjusting the shape wire and fitting it along the desired hair boundaries; tying the two side wires, each of which extends down from the shape wire, so as to keep the shape wire and the two side wires in place on the user's head; draping a shape sheet over the user's head wearing the shape wire and fitting the shape sheet around the user's head and the shape wire fitting along the desired hair boundaries; pinching the portion of the shape sheet along the shape wire fitting over the desired hair boundaries; and taking off the shape wire along with the two side wires and the shape sheet and placing on a domed support pad.

The step of putting the shape wire on the user's head may comprise a step of fixing an overlapped portion of the shape wire and configuring it to hold and prevent the overlapped portion from slipping or loosening with a predetermined resistance and the overlapped portion may be disposed at the rear of the user's head.

The step of tying the two side wires may comprise a step of holding and preventing the overlapped portion from slipping or loosening with a predetermined resistance with two side tubes, each of which being provided around an overlapped portion of the shape wire and one of the side wires, and the overlapped portions may be disposed above the user's ears.

The shape wire may comprise solid metal and twisted strands of two or more solid metal wires. The shape wire may comprise chenille strands.

The two side wires may comprise soft metal, and wherein one of the two side wires comprises iron and copper.

The shape sheet may comprise a malleable metal sheet, and in an embodiment the shape sheet may comprise aluminum foil.

The method may further comprise filling molding material into concave portion of the shape sheet and casting the shape of the user's head and the desired hair boundaries defined by the shape wire.

The advantages of the present invention are: (1) the self-applied measurement kit for a hair replacement mold enables a user to obtain a molding specification for oneself; and (2) the self-applied measurement kit for a hair replacement mold enables a method in which a user, a design coordinator, and a caster can communicate with one another remotely.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

This invention relates to a self-applied measurement kit for a hair replacement mold, which is to create a new method of negative head shape molding without mess and in a time efficient manner. A sheet of aluminum of adequate size, approximately 10"×12", can be draped over and pressed against an individual user's head, molding the aluminum to the shape of the head of the user. The finished and cast mold reveals the user's head size and depth of head shape.

The purpose of the self-applied measurement kit for a hair replacement mold is to create a simple, fast, cost-effective, yet accurate head mold for men and women who are having a customized hair piece made or replaced. The method can be also be used for hair replacement specialists. For the past several decades, making head molds for hair replacement pieces has been one of the key factors in making successful hair replacement products. To date, mold making jobs have been performed solely by trained professionals in the field of hair replacement or enhancement.

A process using rigid sheet material(s) with lines indicating pegs or self-adhering marking stickers enables individuals or professionals to make perfect head molds for purposes of hair replacement, enhancement, or prosthesis.

Traditional methods of mold making are generally classified into two categories: non-rigid tape mold using clear tape or rigid molds using Plaster of Paris, which has been the favored method for experienced hair replacement professionals making high end hair pieces.

Non-Rigid Tape Molds: Tape molds are the most common method simply because they cost less and are relatively easy to make. However, a client cannot create one by his or herself and always requires a skilled hair replacement professional. The process requires a trained hair specialist to place Stretch Wrap (e.g., Seran Wrap) over the client's head, twist the ends of the wrap by pulling tightly to make the wrap wrinkle free, then having the client hold the end wrap tightly. If the client inadvertently loosens the ends of the wrap, the placement of the tape will become inaccurate and it will be impossible to achieve a correct mold. After the wrap is securely held by the client, the hair specialist places transparent tape, e.g., Scotch tape, over the wrap line by line, horizontally once to cover an entire section of bald or thinning area, then vertically once again to form a pattern. After the tape mold is completed, the hair specialist draws first the hairline and then draws a line over the thinning area with a permanent marker. The name of the client and miscellaneous directions can then be written on the mold.

Rigid Plaster Molds: Another mold method uses Plaster of Paris. This method involves a level of complexity such that only experienced and trained hair professionals will have the requisite level of skill and expertise to complete the mold. This method requires sets of fast setting Plaster of Paris, approximately 3"×12"; water; transferable Permanent marker in red color; and a sheet of Stretch Wrap (e.g., Seran Wrap). First, the hair specialist marks the hairline on the client's forehead and applies marks over thin or balding areas by grease or eyebrow pencil. The hair professional then places the stretch wrap over the client's head, pulls it down to make the Wrap wrinkle free and then has the client pull down and hold both ends of the Wrap. Next, the hair professional uses Permanent marker to trace on the Wrap a line along the head showing the hairline and delineating the bald or thinning areas. Next, the hair professional wets the Plaster of Paris one layer at a time and places it over the wrap covering an entire thin or balding area. An additional layer should be applied horizontally and will ensure an accurately formed negative mold. The hair professional then applies heat from a hair dryer for approximately five minutes. This method requires the presence of a hair professional, most likely a hair professional's assistant with training in the technique.

There are other methods available but cost and equipment requirements limit their usage.

Unlike the methods indicated above, a method according to the invention requires only three simple steps. It is not only easy to do by a user of almost any age, but it also can be done entirely by the user, without the need for a hair professional. The method is easy, quick, cheap, but still allows the user to maintain accuracy.

The material cost is approximately one tenth of other methods, primarily because wrap and Plaster is not required. Covering the head in wrap material is not required, saving the user from discomfort. Additionally, the method requires no application of plaster, and thus saves the user from any messes caused by the same. Moreover, with both tape and Plaster of Paris mold methods, recreating the correct line of thinning or balding hairlines becomes difficult as the user cannot see the marking line over hair instead of a bald scalp. This will create problems. However, the invention method can identify the hairline by picking up marked dots inside of the mold.

Figure 1:
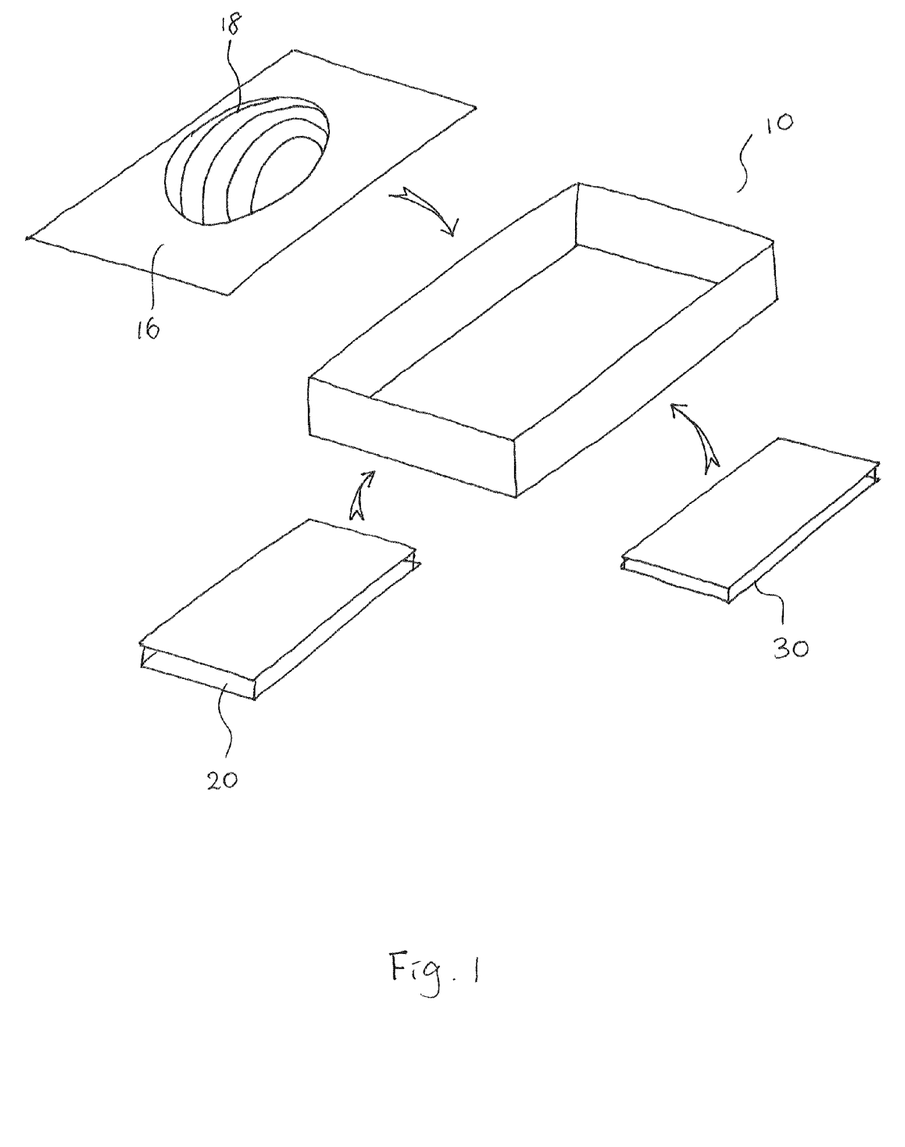
FIG. 1 is a perspective view showing a self-applied measurement kit for a hair replacement mold according to an embodiment of the present invention.

Referring to FIG. 1, the prospective hair piece client receives the hair kit box from a design coordinator, by mail or express. Opening the hair kit box 10, the user will find a dome shaped support pad 15, which includes a molded or otherwise shaped domed region 18 corresponding to the top of the user's head, affixed to the diagonal center of a flat base pad 16 which just fits within the hair kit box 10.

Removing the domed support pad 15, a hair kit manual and questionnaire 20 and a hair kit materials package 30 is underneath. The hair kit manual and questionnaire 20 contains a detailed set of instructions of how to use the hair kit, and a questionnaire to be filled in by the user that will specify how the hair piece is to be constructed. The user-supplied information would include color, hair density by region, and how present remaining hair that is adjacent to the desired hair piece is shaped, such as cut length and hair orientation.

Figures 2, 3:
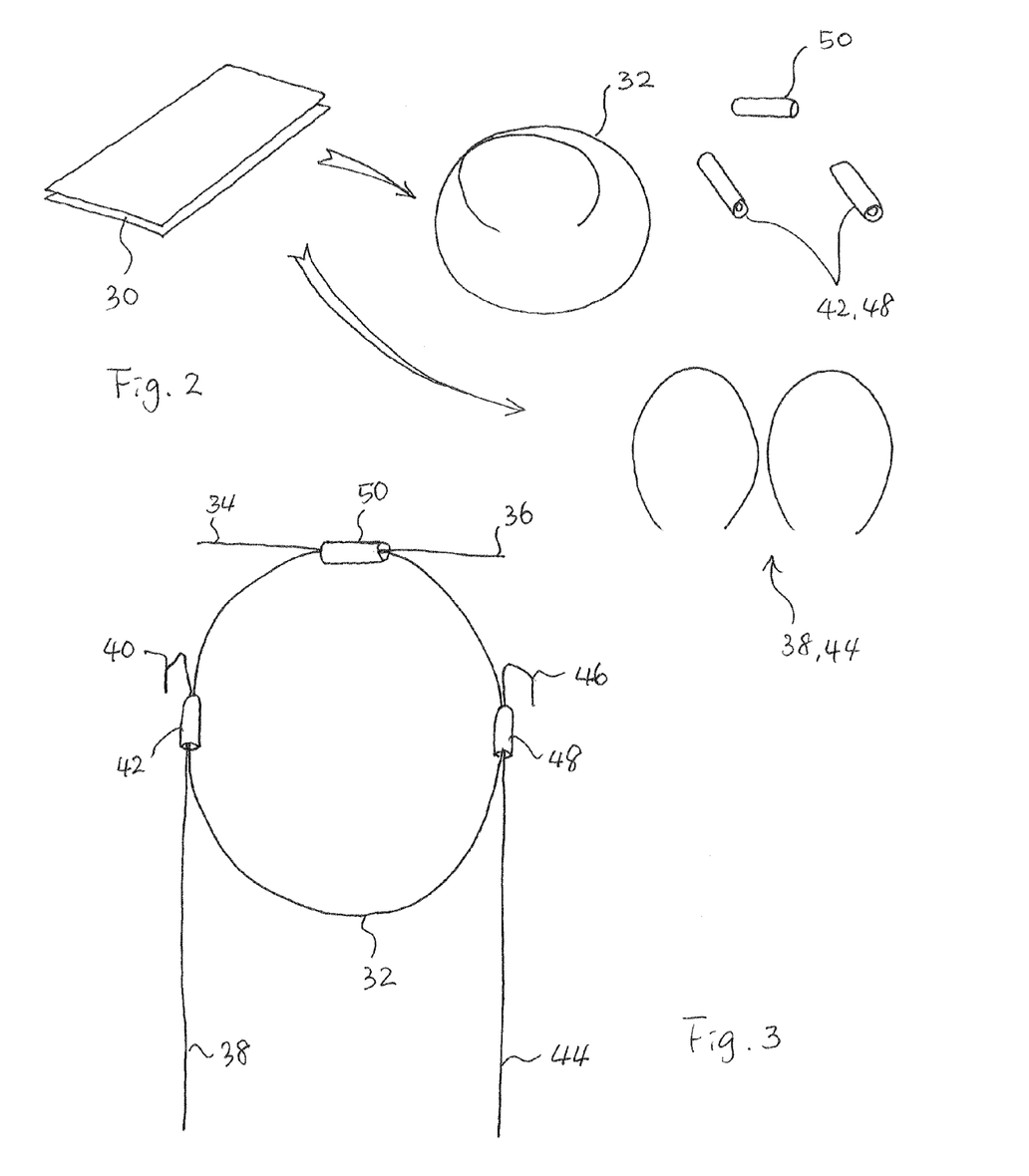
FIG. 2 is a perspective view showing wire kit parts of a self-applied measurement kit for a hair replacement mold according to an embodiment of the present invention.
FIG. 3 is a schematic diagram showing a wire ready for shaping on a user's head.

After the user has read the hair kit manual and set aside the questionnaire 20 for completion, the hair kit materials package 30 may be withdrawn and opened. As shown in FIG. 2, the materials package 30 will contain a coiled length of shape wire 32. This shape wire may be of solid metal, or the twisted product from two wires of solid metal, similar to a "pipe cleaner", and can be supplied with or without the chenille strands, at the wish of the design coordinator. The shape wire 50 would be easily bendable to a shape determined by the user.

The materials package 30 would also contain two side wires 38, 42 including thin soft metal, such as iron or copper, nominally #20 AWG. In the materials package 30 are also some small tubes. A rear tube 50 and side tubes 42, 48 are provided. These are small, somewhat flexible and hollow tubes of plastic, such as polyethylene.

In FIG. 3, wires assembled for use, the user would thread side tubes 42, 48 onto shape wire 32 as shown, and would then thread the shape wire ends 34, 36 through the rear tube 50, so that the shape wire ends protrude from both ends of the rear tube 50. The oval shape of the shape wire 32 may now be adjusted until it approximates a head oval of the user as shown. Side wire 38 is inserted into side tube 42 and a side wire end crook 40 is shaped by the user. The side wire end crook will anchor the side wire 38 to the side tube 42. Similarly, the shape wire 32 now be adjusted until it approximates a head oval of the client as shown. Next, side wire 44 is inserted into side tube 48 and a side wire end crook 46 is again shaped by the user.

Figure 4:
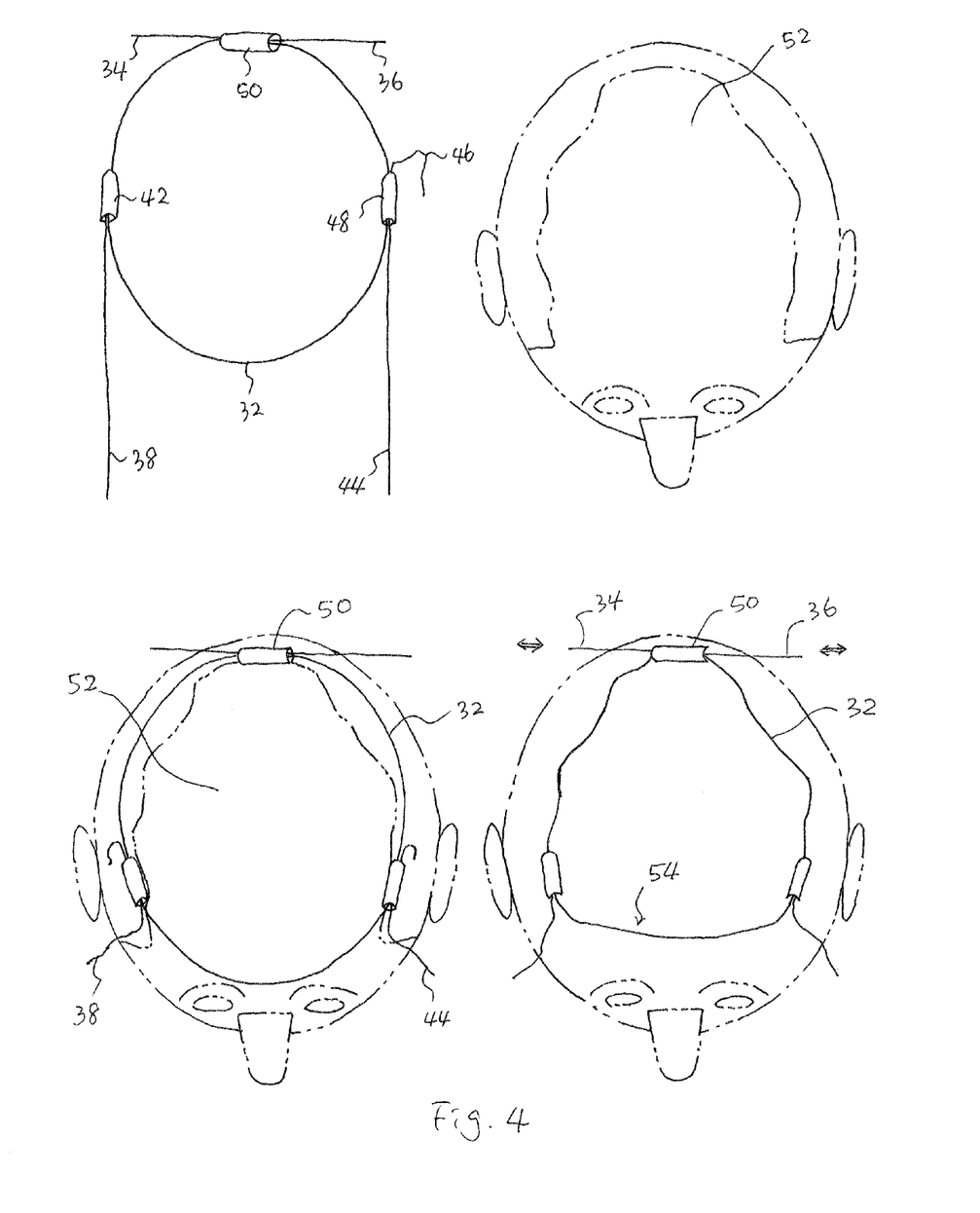
FIG. 4 is a top plan view of a shape wire on the head.

Next, the completed wire ensemble of FIG. 3 is laid atop the user's head 52 as shown. Shape wire 32 may now be adjusted until it approximates a head oval of the user as shown in FIG. 4 showing shape wire placement on head. It is intended that the side wires 38, 44 would drape along the sides of the head 52, just forward of the ears 56, 58 as shown in FIG. 5.

As shown in the lower right portion of FIG. 4 showing shape wire placement on head, the shape wire is carefully adjusted to the boundaries 54 of the desired hair piece. The user is instructed to be very careful in this boundary 54 shape adjustment, as the complete boundary shape will be a fundamental determinant of the shape of the finished hair piece. Once the shape wire 32 has been formed into desired hair boundaries 54, the shape wire ends 34, 36 may be crooked around rear tube 50 so as to help hold the boundaries 54 configuration of shape wire 32 in place. The frontal area of the prospective hair piece is a matter of some concern, and the user will be informed of the logical choices of frontal hair line with regard to sex, age, and to incorporate the styling preferences of the user. If a frontal peak is desired, the shape wire would be formed in the frontal area to reflect this desire, otherwise a gentle curve of the shape wire 32 is sufficient to indicate the desired boundaries 54 in the frontal area as shown.

Once the shape wire 32 has been adjusted to fit the desired hair boundaries 54, the wire ensemble can be tied down for stability. This tie down is accomplished by taking the two side wire 38, 44, and gently twisting them together under the chin 60, as shown in FIG. 5 showing a shape wire tied down. Now the shaped wire ensemble will remain in a stable position on the user's head 52.

Figure 5:
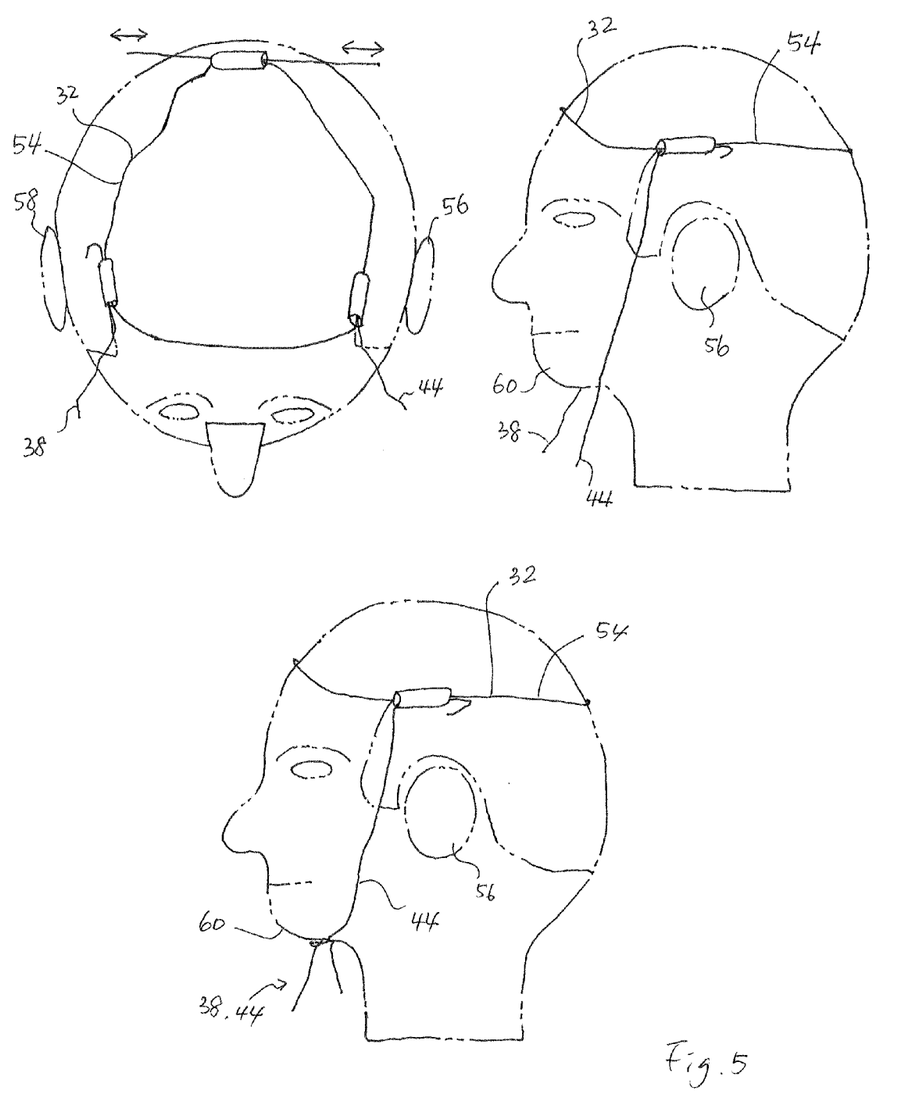
FIG. 5 is a diagram showing a shape wire tied down on the head.
Figure 6:
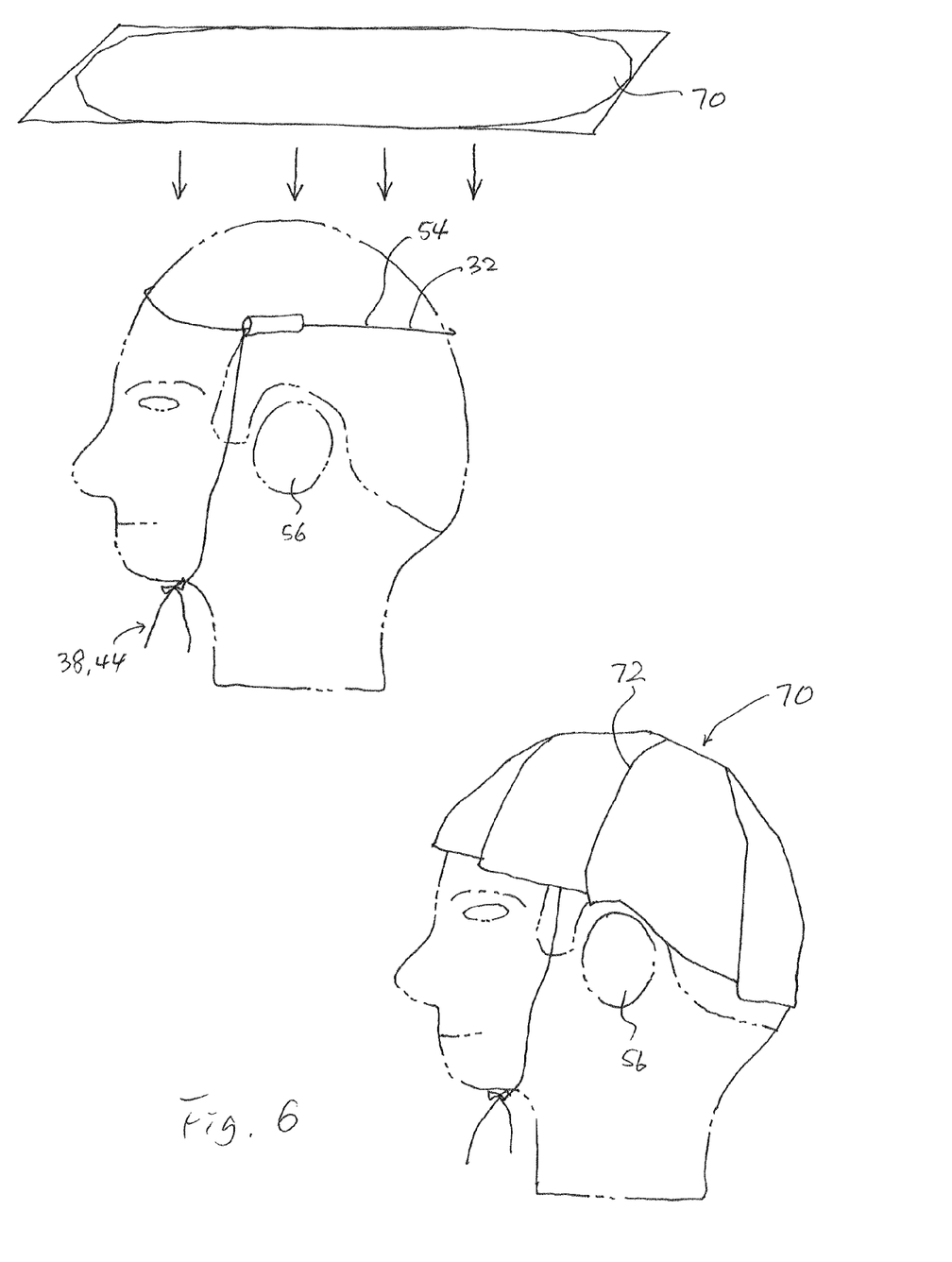
FIG. 6 is a perspective view showing foil placement and shaping.

As shown in FIG. 5 showing foil placement and shaping, the foil sheet 70 is obtained from the hair kit materials package 30. The foil sheet may be rectangular or more commonly, pre-cut into a large oval shape, as shown at upper right in FIG. 5.

Since the twisted side wires 38, 44 are holding the boundary shape wire 52 in place, the foil sheet 70 may be gently placed atop the user's head. The foil 70 will usually be an easily malleable metal sheet, for example, the "heavy duty" aluminum foil used in kitchens. This foil sheet 70 will be gently pressed down overt he head 52 with boundary adjusted shaped wire 54 underneath. Because a flat sheet is being formed into a dome shape, shaping of the foil layer 70 will create creases 72. It is very important that this shaped foil 70 will retain the shape of the user's head 52, and it may be necessary to use a second foil 70 atop the first one to give sufficient body to the constructed shape.

Figure 7:
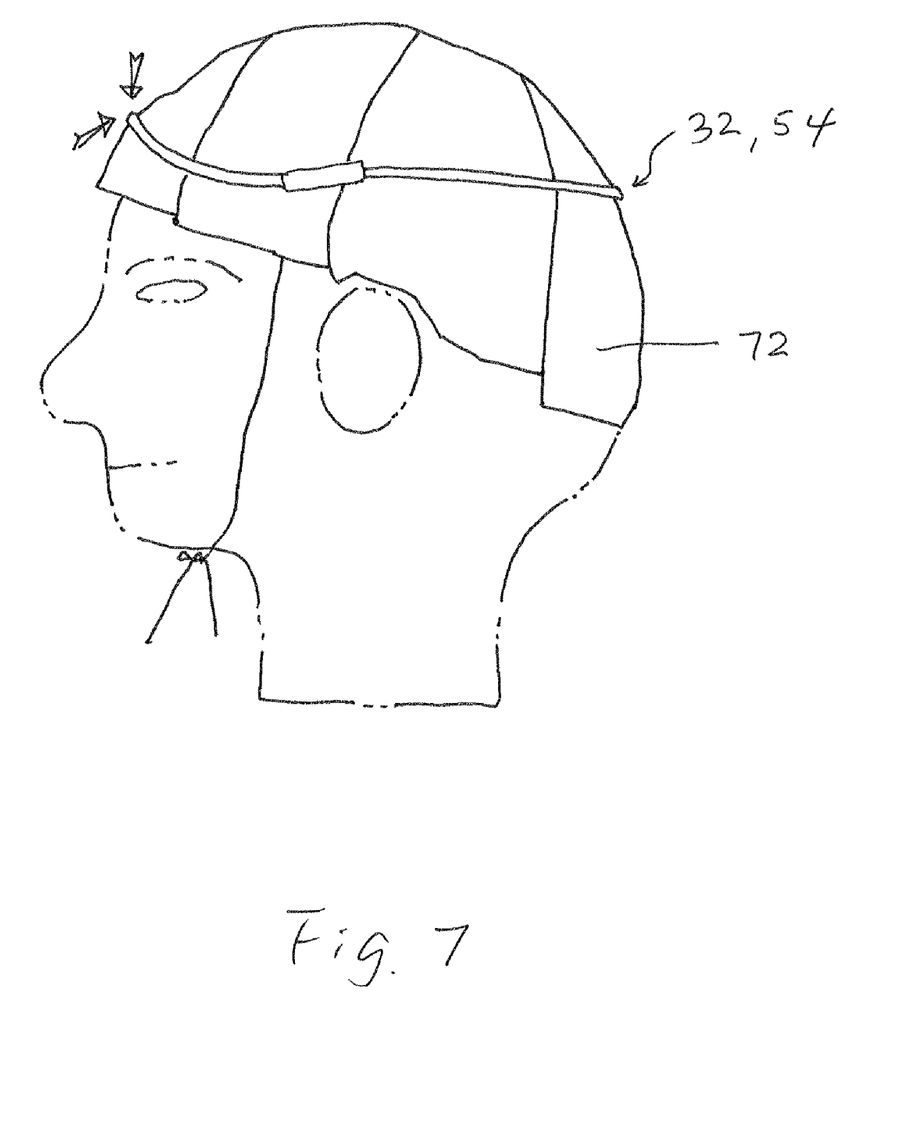
FIG. 7 is a perspective view showing foil pinching for shape transfer.

In FIG. 7 showing a foil pinching for shape transfer, the user is to use thumb and forefinger to form pinching fingers 73, and will pinch 74 along the formed bump 76 representing the formed shape wire 54 underneath the surface of the creased foil sheet 78. This will transfer the route of the boundary shape wire 54 underneath the foil 70 to a shaped bump atop the creased foil 78.

Figure 8:
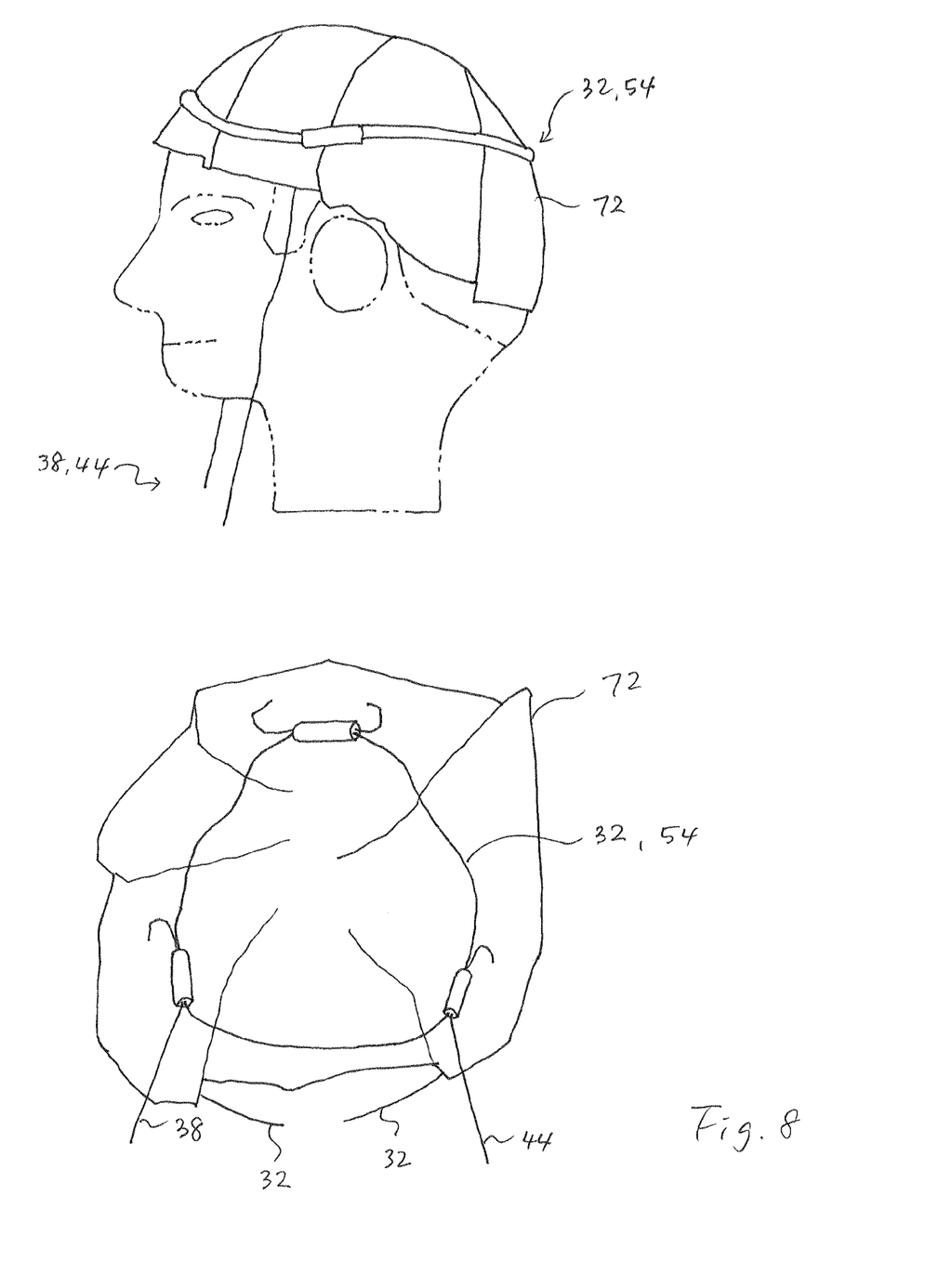
FIG. 8 is a perspective view showing removal of shaped foil.

FIG. 8 shows the removal of shape foil 72 and shaped wire 54 from the head 52. To do this, the side wires 38, 44 are untied from under the chin 50. Now the completed foil and wire ensemble can be gently lifted off the head 52. An interior view of the creased foil 72 as shaped over the head 52 will also show the shape wire 54 in place along the back surface of the dome-shaped creased foil 72. The pinch-formed bump 76 in the foil 78 will retain the boundary shaped wire 54 if the completed foil dome is handled gently.

Figure 9:
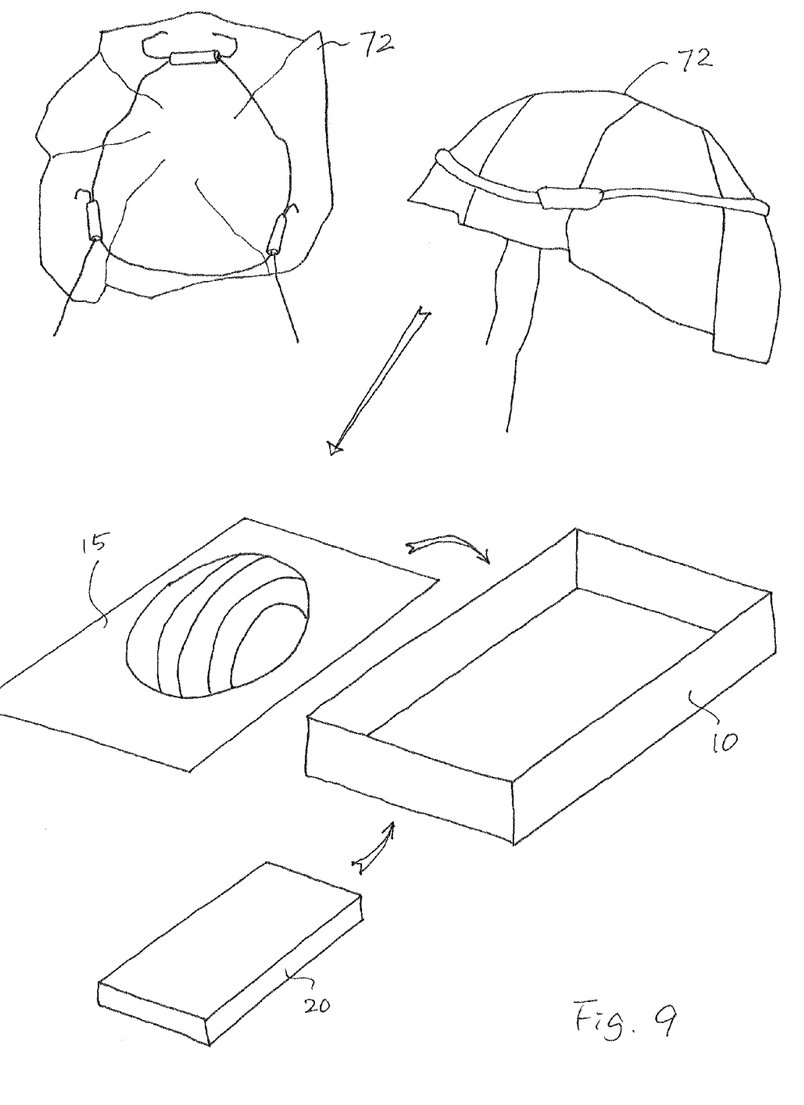
FIG. 9 is a perspective view showing a preparation of shaped foil for return shipping to design coordinator.

FIG. 9 shows the preparation of shaped foil 72 for return shipping to the design coordinator. First, the hair kit manual and completed questionnaire 20 are placed on the bottom of the hair kit box for shipping 10. The shaped foil 72 with shape wire 54 inside is gently placed atop the dome region 18 of the domed support pad 15. The domed support pad 15 is then carefully placed within the hair kit box 10 for shipping. It is likely that the design coordinator will have furnished a return mailing label for the hair kit box.

Figure 10:
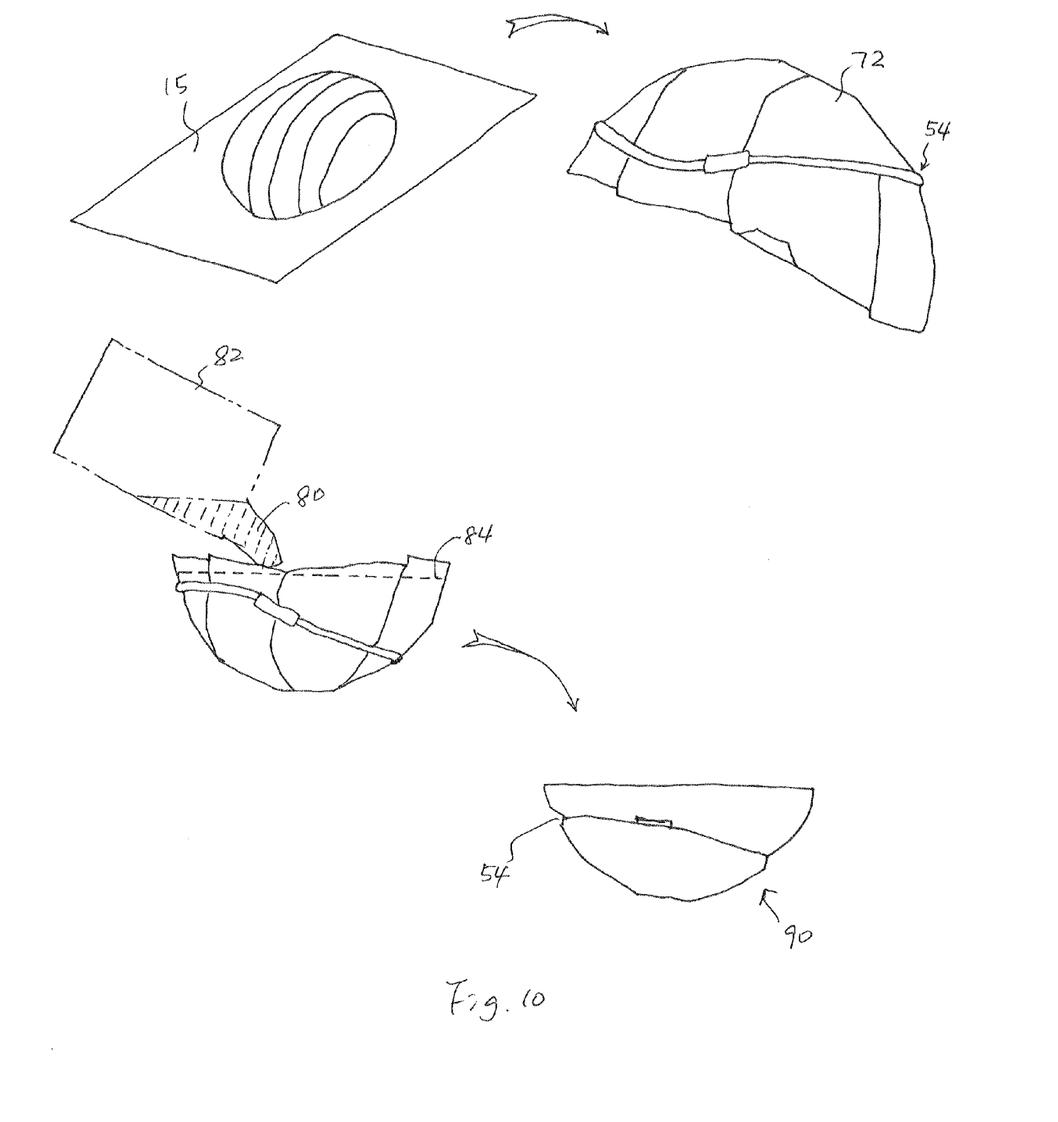
FIG. 10 is a perspective view showings casting of head mold from shaped foil by design coordinator.

As shown in FIG. 10 showing casting of head mold from shaped foil, the design coordinator would gently remove the shaped foil 72 with shape wire 54 inside. A thin layer of mold release would coat the entire interior of shaped foil 72, including the shape wire 54.

Next, molding material 80 would be mixed and placed in molding material container 82. The molding material 80 would be poured into the inverted shaped foil 54 dome. The molding material would fill the shaped foil 54 dome to the "fill to" line 84 shown.

The poured mold would be set aside to cure. After curing, the shaped foil 72 with shaped wire 54 inside would be removed from the finished casting 90. Note that the shape wire's location 54 will cause a clearly visible indentation in finished casting 90.

The choice of molding material is determined by the design coordinator, depending on what preparation steps may be needed for the finished casting to facilitate best communication with the hair piece fabricator. For instance, a filler material such as sawdust may be included in the molding material to facilitate placement of push pins during hair piece manufacture.

An aspect of the invention provides a self-applied measurement kit for a hair replacement mold.

The self-applied measurement kit for a hair replacement mold comprises a shape wire, two side wires, one shape sheet and one domed support pad.

The shape wire is configured to be adjusted to fit the desired hair boundaries on a user's head and to be fixed.

The two side wires, each of which extend downward from a side portion of the shape wire, are configured to be draped downward and tied down under the chin of the user, so as to fix the shape wire in place to the user's head.

The shape sheet is configured to cover the user's head wearing the shape wire, so as to imprint the shape of the head, and the shape sheet is pinched over the shape wire so as to imprint the position and shape of the shape wire.

The domed support pad is configured to support and keep the molded shape wire and shape sheet from deforming.

The two side wires facilitate fixing the shape wire to the user's head and the shape wire imprints the shape of the head and the desired hair boundaries on the shape sheet. The shape wire may comprise solid metal and twisted strands of two or more solid metal wires. In certain embodiments of the invention, the shape wire may comprise chenille strands.

The two side wires may comprise soft metal. In certain embodiments of the invention, one of the two side wires may comprise iron and copper.

The shape sheet may comprise malleable metal sheet. In certain embodiments of the invention, the shape sheet may comprise aluminum foil.

The self-applied measurement kit may further comprise a rear tube provided around an overlapped portion of the shape wire and configured to hold and prevent the overlapped portion from slipping or loosening with a predetermined resistance.

The overlapped portion may be disposed at the rear of the user's head.

The self-applied measurement kit may further comprise two side tubes, each of which being provided around an overlapped portion of the shape wire and one of the side wires and configured to hold and prevent the overlapped portion from slipping or loosening with a predetermined resistance. The overlapped portions may be disposed of above the user's ears.

Another aspect of the invention provides a method for self-applied measurement for a hair replacement mold.

The method comprises steps of: putting a shape wire on a user's head; adjusting the shape wire and fitting along desired hair boundaries; tying two side wires, each of which extends down from the shape wire, so as to keep the shape wire and the two side wires in place on the user's head; draping a shape sheet over the user's head wearing the shape wire and fitting the user's head and the shape wire fitting along the desired hair boundaries; pinching the portion of the shape sheet along the shape wire fitting over the desired hair boundaries; and taking off the shape wire along with the two side wires and the shape sheet and placing on a domed support pad.

The step of putting a shape wire on a user's head may comprise a step of fixing an overlapped portion of the shape wire that is configured to hold and prevent the overlapped portion from slipping or loosening with a predetermined resistance, and the overlapped portion may be disposed at the rear of the user's head.

The step of tying may comprise a step of holding and preventing the overlapped portion from slipping or loosening with a predetermined resistance with two side tubes, each of which being provided around an overlapped portion of the shape wire and one of the side wires, and the overlapped portions may be disposed above the user's ears.

The shape wire may comprise solid metal and twisted strands of two or more solid metal wires. The shape wire may comprise chenille strands.

The two side wires may comprise soft metal, wherein one of the two side wires comprises iron and copper.

The shape sheet may comprise a malleable metal sheet, and in an embodiment the shape sheet may comprise aluminum foil.

The method may further comprise filling molding material into a concave portion of the shape sheet and casting the shape of the user's head and the desired hair boundaries defined by the shape wire.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A self-applied measurement kit for a hair replacement mold comprising:
   one shape wire configured to be adjusted to fit desired hair boundaries on a user's head and to be fixed;
   two side wires, each of which extend downward from a side portion of the shape wire, configured to be draped downward and tied down under a chin of the user, so as to fix the shape wire in place on the user's head;
   one shape sheet configured to cover the user's head wearing the shape wire, so as to imprint the shape of the head, wherein the shape sheet is pinched over the shape wire so as to imprint position and shape of the shape wire; and
   one domed support pad configured to support and keep the shaped shape wire and shape sheet from deforming,
   wherein the two side wires facilitate fixing the shape wire to the user's head wherein the shape wire imprints the shape of the head and the desired hair boundaries on the shape sheet.

2. The self-applied measurement kit of claim 1, wherein the shape wire comprises solid metal and twisted strand of two or more solid metal wires.

3. The self-applied measurement kit of claim 2, wherein the shape wire comprises chenille strands.

4. The self-applied measurement kit of claim 1, wherein the two side wires comprise soft metal.

5. The self-applied measurement kit of claim 4, wherein one of the two side wires comprises iron and copper.

6. The self-applied measurement kit of claim 1, wherein the shape sheet comprises malleable metal sheet.

7. The self-applied measurement kit of claim 6, wherein the shape sheet comprises aluminum foil.

8. The self-applied measurement kit of claim 1, further comprising a rear tube provided around an overlapped portion of the shape wire and configured to hold and prevent the overlapped portion from slipping or loosening with a predetermined resistance.

9. The self-applied measurement kit of claim 8, wherein the overlapped portion is disposed at the rear of the user's head.

10. The self-applied measurement kit of claim 1, further comprising two side tubes, each of which being provided around an overlapped portion of the shape wire and one of the side wires and configured to hold and prevent the overlapped portion from slipping or loosening with a predetermined resistance.

11. The self-applied measurement kit of claim 10, wherein the overlapped portions are disposed above the user's ears.

12. A method for self-applied measurement for a hair replacement mold that comprising steps of:
putting a shape wire on a user's head;
adjusting the shape wire and fitting along desired hair boundaries;
tying two side wires, each of which extends down from the shape wire, so as to keep the shape wire and the two side wires in place on the user's head;
draping a shape sheet over the user's head wearing the shape wire and fitting the user's head and the shape wire fitting along the desired hair boundaries;
pinching the portion of the shape sheet along the shape wire fitting over the desired hair boundaries; and
taking off the shape wire along with the two side wires and the shape sheet and placing on a domed support pad.

13. The method of claim 12, wherein the step of taking off comprises a step of fixing an overlapped portion of the shape wire and configured to hold and prevent the overlapped portion from slipping or loosening with a predetermined resistance, and wherein the overlapped portion is disposed at the rear of the user's head.

14. The method of claim 12, wherein the step of tying comprises a step of holding and preventing the overlapped portion from slipping or loosening with a predetermined resistance with two side tubes, each of which being provided around an overlapped portion of the shape wire and one of the side wires, and wherein the overlapped portions are disposed above the user's ears.

15. The method of claim 12, wherein the shape wire comprises solid metal and twisted strands of two or more solid metal wires.

16. The method of claim 15, wherein the shape wire comprises chenille strands.

17. The method of claim 12, wherein the two side wires comprise soft metal, and wherein one of the two side wires comprises iron and copper.

18. The method of claim 12, wherein the shape sheet comprises malleable metal sheet, and wherein the shape sheet comprises aluminum foil.

19. The method of claim 12, further comprising filling molding material into concave portion of the shape sheet and casting the shape of the user's head and the desired hair boundaries defined by the shape wire.

* * * * *